United States Patent [19]

Leach

[11] Patent Number: 5,397,171
[45] Date of Patent: Mar. 14, 1995

[54] GAIT ASSISTANCE HARNESS APPARATUS

[76] Inventor: Dana M. Leach, 129 Puritan Rd., Buzzards Bay, Mass. 02532

[21] Appl. No.: 103,544

[22] Filed: Aug. 9, 1993

[51] Int. Cl.$^6$ .......................... A61H 3/00; B60R 22/00
[52] U.S. Cl. .................... 297/484; 297/485; 128/875
[58] Field of Search ......... 297/183, 484, 485, DIG. 4; 128/845, 846, 870, 875, 876; 5/81.1, 89.1

[56] References Cited

U.S. PATENT DOCUMENTS

| | | | |
|---|---|---|---|
| 1,288,170 | 12/1918 | Pick | 297/484 |
| 1,326,716 | 12/1919 | Dunning | 297/484 |
| 3,182,338 | 5/1965 | Shirrod | |
| 3,466,090 | 9/1969 | Posey | 297/484 |
| 5,263,495 | 11/1993 | Butterfield | 128/875 X |

FOREIGN PATENT DOCUMENTS

| | | | |
|---|---|---|---|
| 441837 | 1/1968 | Switzerland | 297/484 |
| 114104 | 3/1918 | United Kingdom | 297/484 |
| 180866 | 6/1922 | United Kingdom | 297/484 |

Primary Examiner—Peter R. Brown
Attorney, Agent, or Firm—Richard P. Crowley

[57] ABSTRACT

A gait assistance harness apparatus for help by a therapist of a patient user in walking and preventing accidental falls is described. The apparatus comprises a gait belt to encircle the waist of a patient, a belt handle means on the rear section of the gait belt, and a shoulder harness means securely attached to the gait belt. Shoulder handle means located on and aligned with each shoulder harness strap, and, in use, positioned on the upper shoulder back section of the shoulder harness means, provide an apparatus by which a therapist can catch a patient in danger of falling, and can assist the patient user in walking therapy. Upper extremities support rings positioned on the front face of each shoulder harness strap and a waist support ring positioned on each side of the gait belt permit the insertion of restraining straps to secure a patient user in an upright seated position in a wheelchair or other article of furniture.

13 Claims, 3 Drawing Sheets

GAIT ASSISTANCE HARNESS APPARATUS

BACKGROUND OF THE INVENTION

Broken bones, fractures and sprains in the human body often require that a patient spend recuperative time learning to be ambulatory. In many cases, a patient must be taught how to walk, climb and descend steps, and generally to maneuver successfully on mechanical supports, or simply to learn to walk by practice on a treadmill-type device or with the help of another person. Therefore, physical therapists must be trained in the use of methods of teaching ambulation to patients and in the methods of avoiding falls or accidents by patients during this training period.

Therapists have had few assistive apparati to use during periods of patient ambulatory training. The apparatus most utilized is a gait belt which is placed around the waist of a patient. A gait belt usually has two or three handles attached to its back and side sections. If a patient begins to fall during a physical therapy training session, the therapist grasps a handle on the gait belt, thereby hoping to prevent the fall entirely or to control the fall so that the patient does not suffer injury. The patient then is assisted to regain a correct position to continue practicing ambulatory patterns.

At best the use of the handles on a gait belt can be clumsy and ineffective if both patient and therapist are caught in an off-centered position. The therapist must maintain a strong stride position for the balance of both himself and his wobbly patient. Still, the therapist has no way to restrain the upper body of a patient in a falling situation except to grasp at the patient's shoulder in an attempt to slow the rate of falling. If the therapist is unsuccessful, the patient could suffer broken bones or additional bruises.

What is needed is an apparatus that would provide more control for a physical therapist teaching ambulation to a patient. It would be desirable for such an apparatus to be lightweight and comfortable for a patient to wear, sturdy enough to control the weight of a falling adult, and relatively inexpensive to purchase. It would also be desirable for the apparatus to provide a number of handles at key points which a physical therapist could quickly grasp to restrain a falling patient.

SUMMARY OF THE INVENTION

The present invention relates to gait assistance apparati for patients learning to walk with and without the aid of mechanical supports. In particular, the invention relates to a gait belt assistance harness apparatus that provides increased control for a physical therapist teaching a patient dependent on crutches a proper ambulatory gait.

The invention comprises a gait belt that is worn about the waist of a patient user, and a shoulder harness means worn by a patient user in suspender-like fashion. The gait belt has a front section and a rear section, and is provided with an adjustable closure to secure the gait belt in use. Belt handle means on the rear section of the gait belt permit a therapist to assist a patient in walking.

The shoulder harness means comprises first and second shoulder harness straps, each shoulder harness strap having a one end, an other end and a face section. The one end of the first and second shoulder harness straps is securely attached to the rear section of the gait belt, while the other end of the first and second shoulder harness straps is detachably attached to the front section of the gait belt to form a shoulder harness. Shoulder handle means located on and aligned with the first and second shoulder harness straps are, in use, positioned generally on the upper back shoulder area of a patient user and provide a therapist with handles to grasp to prevent a fall by a patient user.

The outer central rear portion of the gait belt has attached handles oriented for use by a therapist in assisting a patient learning to walk. A waist support ring is located on each side of the gait belt at a point approximately one-half the distance between the center rear section and the front section adjustable closure. In a preferred embodiment, the waist support rings are "D rings" which permit the insertion of restraining straps for patient user waist and pelvic support. Such restraining straps are attached at one end to waist support rings on the gait belt worn by the patient user, and at the other end to, for example, a chair in which the patient user is seated.

In a preferred embodiment of the invention, the gait belt is constructed of about a 3 to 4-inch wide, lightweight, sturdy, webbed material. The inner side of the gait belt that lies against the waist of a patient is lined with about a ¼-inch thick piece of neoprene polymer for comfort and support. An adjustable closure on the gait belt preferably consists of a "D ring" belt buckle coupled with a "velcro"-type strip for additional tightening, although any type of closure may be used. An additional strip of webbed material about 1.5 to 2 inches wide may be attached to the outside central front and side sections of the gait belt to provide reinforcing strength and a site of attachment for the adjustable closure. On the upper rim of the gait belt and on either side of the adjustable closure is an interlocking buckle female part adapted to receive a complementary buckle male part which is attached to the front section of the first and second shoulder harness straps of the shoulder harness apparatus.

An adjustable suspender-like shoulder harness apparatus attached to the gait belt provides support and control for the upper extremities of a patient user. In a preferred embodiment of the invention, the shoulder harness comprises first and second shoulder harness straps of lightweight, sturdy, webbed material about 1.5 to 2 inches in width. The first and second shoulder harness straps are attached to the central rear section of the gait belt preferably by stitching, although any means of secure attachment is acceptable. The back sections of the first and second shoulder harness straps are crossed and secured together to form a strap crossover section that, in use, lies against the back of the patient user.

Shoulder harness strap handles are attached to and aligned with the base of both the first and second shoulder harness straps. In a preferred embodiment, the first and second shoulder harness strap handles are made from the same lightweight, sturdy, webbed material as are the first and second shoulder harness straps, and, in use, are positioned generally on the upper back shoulder areas of a patient user. This placement permits a therapist to grasp either the first or second shoulder harness strap handles in combination with either the horizontal belt handle 24 or one of the vertically positioned handles 26 and 28 in order to prevent a fall of a patient being assisted. The inner sides of the first and second shoulder harness straps in the general area overlying the shoulders of a patient user are padded, preferably with about a ¼-inch thick material such as, for example, foam rubber or neoprene for patient comfort and non-slippage.

On the front face section of the first and second shoulder harness straps is an upper extremities support ring such as, for example, a "D ring." These support rings permit a restraining strap to be inserted through them, and the opposite end of the restraining strap to be secured to a wheelchair or other piece of furniture in which a patient is placed in order to maintain a patient user in an upright position.

The front section of the first and second shoulder harness straps also are each equipped with an adjustable clip to accommodate longer and shorter body torso lengths and to provide a patient user with a safe, comfortable fit for the shoulder harness. Interlocking buckle male insert parts are attached to the ends of the front sections of the first and second shoulder harness straps for connection with female receiving parts of the interlocking buckle located on the front rim of the gait belt.

The simplicity of attachments such as the interlocking buckles and adjustable shoulder harness straps permit quick and easy placement and removal of the invention on a patient user, and thereby encourages its use. The gait assistance harness apparatus may be used in any variety of ways by physical therapists in assisting patient users who are learning to walk.

The gait assistance harness apparatus, by virtue of its attached ring supports to maintain waist, pelvis, and upper extremities in their proper positions, is also useful in hospitals, convalescent homes and rehabilitation centers. Bodily support of this nature is especially helpful for elderly patients confined to wheelchairs and for patients of any age who suffer spinal disorders or injuries like muscular dystrophy and paraplegia, for example.

The invention will be described for the purposes of illustration only in connection with certain embodiments. However, it is recognized that those skilled in the art may make various modifications, changes, additions and improvements to the certain embodiments, all falling within the spirit and scope of the invention.

DESCRIPTION OF THE EMBODIMENTS

Figure 1:
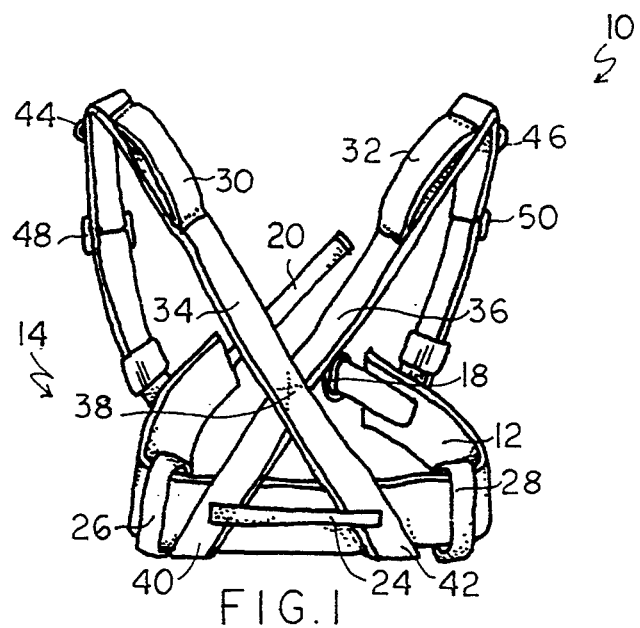
FIG. 1 is a rear perspective view of the gait assistance harness apparatus invention in a gait belt-opened position.

The gait assistance harness apparatus 10 of FIG. 1 comprises a gait belt 12 and a harness apparatus 14. The gait belt 12 is made of sturdy, lightweight, webbed material. An adjustable closure 16 formed by a ring member 18 and a "velcro"-type tape member 20, the latter being adjustable to fit many waist sizes, is located at the front section of the gait belt 12.

Figure 2:
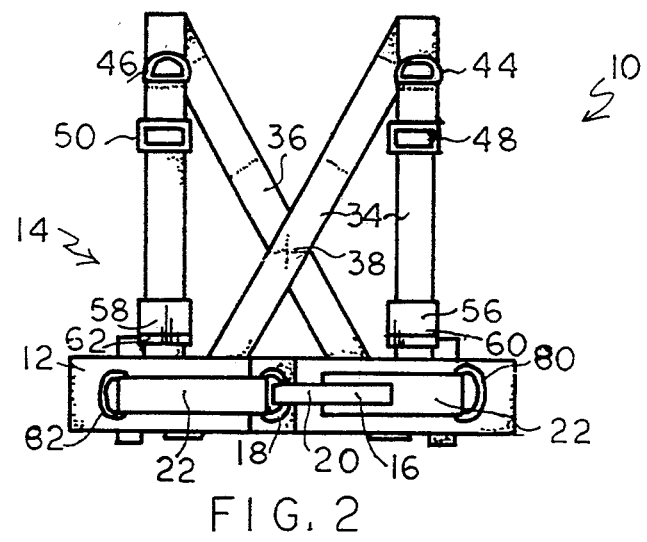
FIG. 2 is a front perspective view of the apparatus of FIG. 1 in a gait belt-closed position.

FIGS. 1 and 2 show another piece of lightweight, sturdy, webbed material that forms a thin belt 22 attached to the front section of the gait belt 12. This thin belt 22 provides support and a point of attachment for the ring member 18 and the "velcro"-type tape member 20 of the adjustable closure 16.

FIG. 1 best illustrates the gait assistance harness apparatus handles which a physical therapist can grasp to assist a patient user in walking and to catch a patient user who is falling. A horizontal belt handle 24 is shown secured to the rear center section of the gait belt 12. This horizontal belt handle 24 is useful for a therapist guiding the ambulatory attempts of a patient user and preventing a patient from falling. On either side of the horizontal belt handle 24 on the rear section of the gait belt 12 are shown vertically positioned handles 26 and 28. These vertically positioned handles are also for use by a physical therapist to grasp the gait assistance harness apparatus to assist a patient user.

Figure 4:
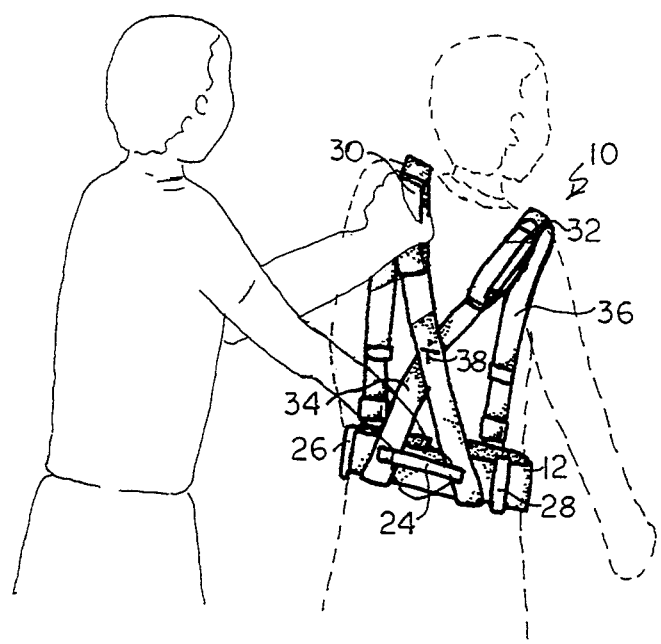
FIG. 4 is a rear perspective view of the apparatus of FIG. 1 as worn by a patient user and assisted by a therapist.

Another pair of handles, the first and second shoulder harness strap handles 30 and 32, appear on the back section of the shoulder harness straps 34 and 36 of the harness apparatus 14. The first and second shoulder harness strap handles 30 and 32 are made of the same sturdy, lightweight, webbed material as are the gait belt 12 and the shoulder harness straps 34 and 36. These first and second shoulder harness strap handles 30 and 32 are attached to and aligned with the base of the shoulder harness straps 34 and 36. FIG. 4 shows the first and second shoulder harness strap handles 30 in use by a therapist. The first and second shoulder harness strap handles 30 and 32 are positioned, in use, generally on the upper back shoulders of a patient user in order to permit a therapist to grasp either the first or second shoulder harness strap handles 30 and 32 in combination with either the horizontal belt handle 24 or one of the vertically positioned handles 26 and 28 as a means of preventing a fall by a patient user.

FIG. 1 also shows a strap crossover section 38 formed by the crossing and securing together of the first and second shoulder harness straps 34 and 36 in the back section of the harness apparatus 14. FIG. 4 shows that the strap crossover section 38 is, in use, generally positioned against the center back of a patient user to provide a firm fit for the harness apparatus 14. FIG. 1 best illustrates the attachment of the ends 40 and 42, the one ends, of the first and second shoulder harness straps 34 and 36 respectively to the rear section of the gait belt 12.

FIG. 2 is a front perspective view of the gait assistance harness apparatus with the adjustable closure 16 in a closed position. Visible in FIG. 2 are the ring member 18 and the "velcro"-type tape member 20 of the adjustable closure 16, as well as the thin belt 22 that provides support and a point of attachment for the adjustable closure 16 and is firmly attached to the front section of the gait belt 12.

Figure 5:
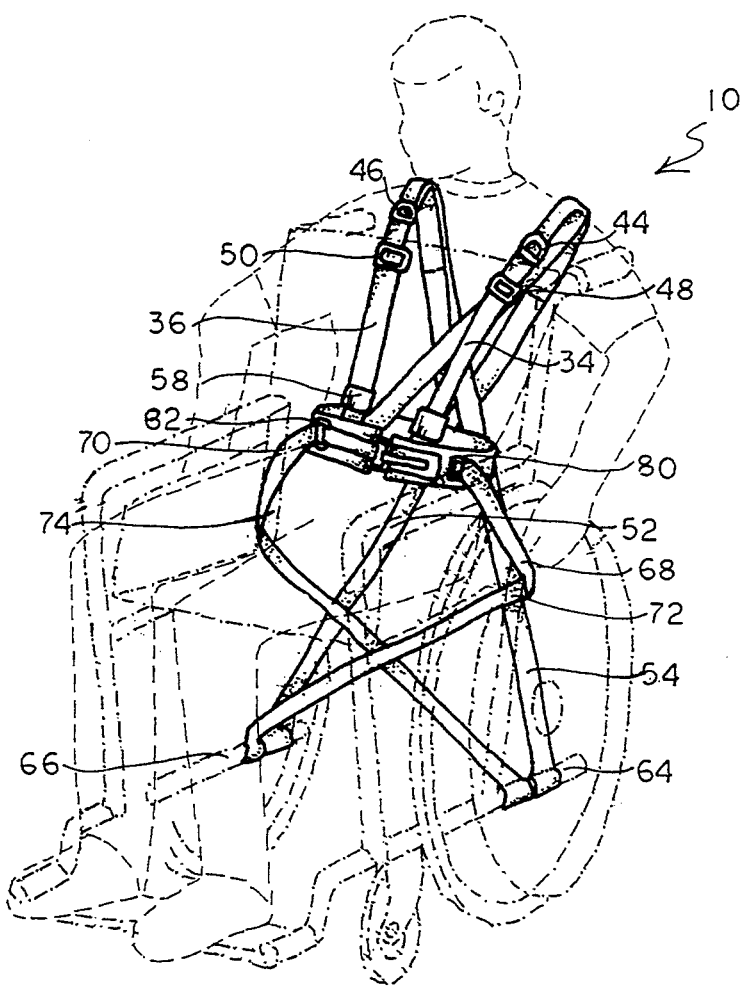
FIG. 5 is a front perspective view of the gait assistance harness apparatus invention worn by a patient user in a wheelchair with restraining straps properly secured.
Figure 6:
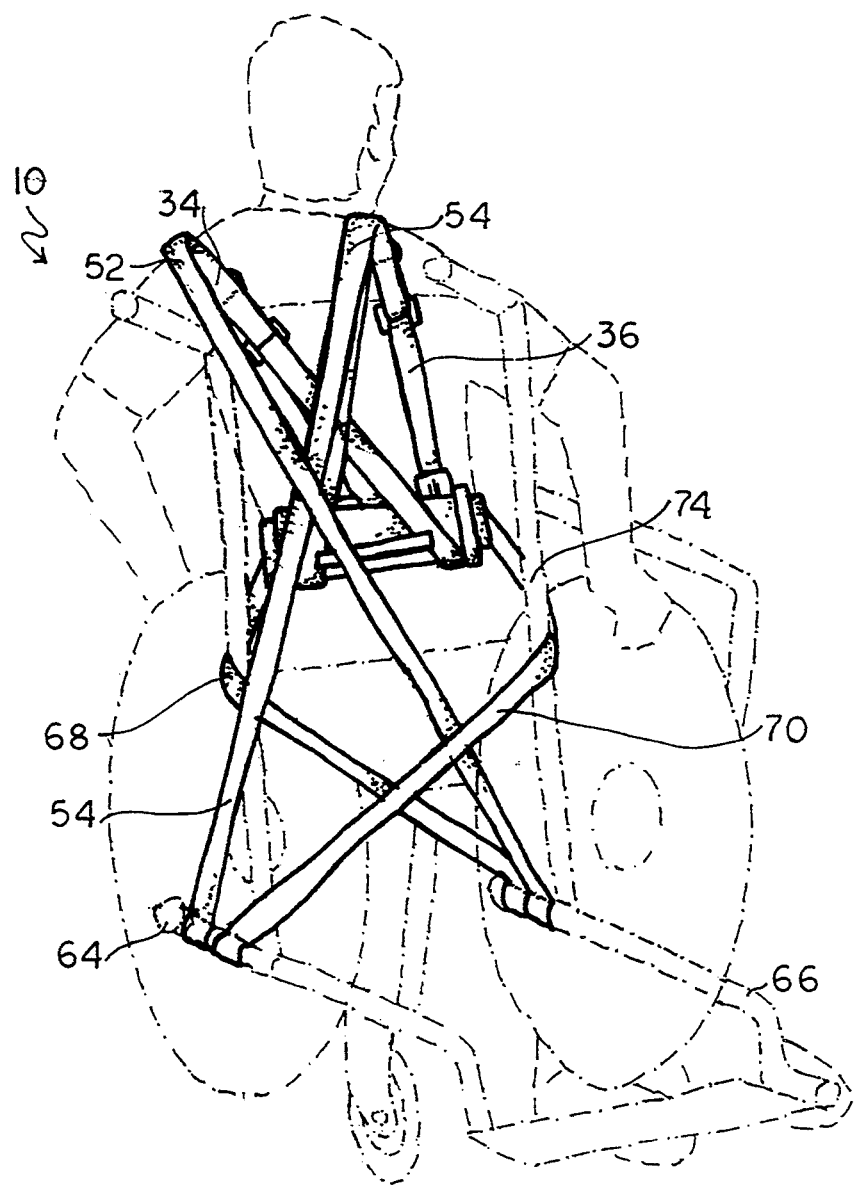
FIG. 6 is a rear perspective view of FIG. 5.

FIG. 2 also shows first and second upper extremities support rings 44 and 46, located on the front faces of the first and second shoulder harness straps 34 and 36 respectively. FIG. 5 shows that, in use, the first and second upper extremities support rings 44 and 46 are positioned near the front shoulders of a patient user and contain restraining straps 52 and 54 which are secured at their opposite ends to a wheelchair or to any other means for holding a patient.

FIG. 2 best illustrates the adjustable clips 48 and 50 on the front faces of the first and second shoulder harness straps 34 and 36 respectively, for lengthening and shortening the first and second shoulder harness straps 34 and 36 in order to accommodate a variety of body torso lengths. The adjustable clips 48 and 50 are positioned between the upper extremities support rings 44 and 46 and the interlocking buckles 56 and 58.

At the front sections of the first and second shoulder harness straps 34 and 36 near the gait belt 12 are interlocking buckles 56 and 58. Each interlocking buckle 56 and 58 comprises an identical male part 60 located at the end of each harness strap 34 and 36, and an identical female part 62 positioned at the upper rim of the gait belt 12. Connection of the male part 60 and the female part 62 affects a coupling of the first and second shoulder harness straps 34 and 36 to the gait belt 12, thereby forming the gait assistance harness apparatus 10.

Figure 3:
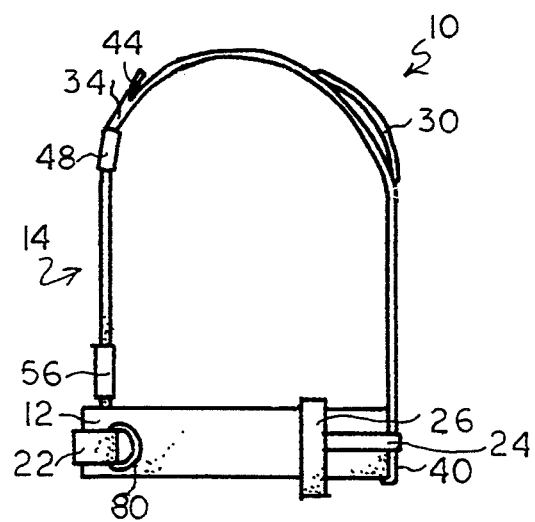
FIG. 3 is a side elevation view of the apparatus of FIG. 1.

FIG. 3 is a side elevation view of the gait assistance harness apparatus invention 10. Readily visible are: a shoulder harness strap handle 30, a belt handle 26, a portion of the thin belt member 22, a back section of the shoulder harness strap 34 and a front section of the shoulder harness strap 36, upper extremities support ring 44, adjustable clip 48 of a shoulder harness strap, interlocking buckle 56, first waist support ring means 80, and the gait belt 12.

FIG. 5 shows the gait assistance harness apparatus invention in use by a patient user seated for example, in a wheelchair. First and second restraining straps 52 and 54 are attached at one of their two ends at the upper extremities support rings 44 and 46 respectively, then are brought over the shoulders from front to back of a patient user, and are brought diagonally down across the back portion of the seat of the wheelchair to be finally secured on their opposite ends to wheelchair support bars 64 and 66. The effect of the restraining straps 52 and 54 is to maintain a patient in an upright position within a seat.

First and second waist support rings 80 and 82, located on either side of the gait belt 12, each hold one end of the third and fourth restraining straps 68 and 70 respectively. The third and fourth restraining straps 68 and 70 then encircle wheelchair support posts 72 and 74, and cross diagonally under the seat of the wheelchair to have their free ends secured to wheelchair supports 64 and 66. Use of the waist support rings 80 and 82 provides proper waist and pelvic support to the patient user.

What is claimed is:

1. A gait assistance harness apparatus for the assistance of a patient user by a therapist which apparatus comprises:
   a) a gait belt to encircle the waist of a patient user and having a front and rear section, an adjustable closure means to secure the gait belt in use, and separate strap belt handle means secured to the rear section of the gait belt to permit a therapist to grasp by hand the belt handle means and to assist a patient user in walking;
   b) a shoulder harness means to be worn by the patient user and which harness means comprises first and second shoulder harness straps each having a first and second end and a face section, the first and second ends of the first and second shoulder harness straps secured respectively to the front and back sections of the gait belt to form a shoulder harness; and
   c) a separate strap shoulder handle means secured to each shoulder harness strap and positioned generally on the rear upper shoulder area of the harness strap to permit a therapist to grasp each separate strap shoulder handle means or, optionally, to grasp with one hand one shoulder handle means and with the other hand to grasp the separate strap belt handle means secured to the gait belt, to prevent the fall of a patient user being assisted.

2. The apparatus of claim 1 wherein the gait belt includes a pair of vertical extending, separate, spaced apart strap belt handle means positioned on and secured to the rear section of the gait belt.

3. The apparatus of claim 1 wherein the shoulder harness means includes the first and second shoulder harness straps with said straps crossed and secured together in the back section to form a strap crossover section.

4. The apparatus of claim 3 wherein the apparatus comprises a webbing material and the first and second separate straps shoulder harness handle means comprise loops of webbing material aligned with the shoulder harness straps.

5. The apparatus of claim 4 wherein the shoulder harness means extends downwardly from about the upper shoulder of the patient user toward the crossover section.

6. The apparatus of claim 1 which includes first and second upper extremities support ring means respectively on the face sections of the first and second shoulder harness straps and positioned in use on the front upper shoulder portion of the shoulder harness to permit a restraining strap to be inserted therethrough and secured to a chair to maintain a patient user in an upright seated position.

7. The apparatus of claim 6 which includes a strap means for insertion through the ring means.

8. The apparatus of claim 6 which includes first and second waist support ring means each secured respectively on either side of the gait belt to permit the insertion of a waist restraining strap therethrough to retain a patient user in a chair.

9. The apparatus of claim 8 which includes a waist restraining strap for use with the waist support ring means.

10. The apparatus of claim 1 wherein the gait belt includes a horizontally extended, separate strap belt handle means centrally positioned and secured to the rear section of the gait belt.

11. A gait assistance harness apparatus for the aid of a patient user by a therapist which includes:
   a) a gait belt to encircle the waist of a patient user and having a front section and a rear section;
   b) an adjustable closure means to secure the gait belt in use around the waist of a patient;
   c) separate strap, belt handle means on and secured to the rear section of the gait belt to permit a therapist to assist a patient in walking;
   d) a shoulder harness strap means having adjustable first and second shoulder harness straps, each strap having a first end and a second end, a face section and a back section;
   e) a separate strap shoulder handle means located on and aligned with each adjustable shoulder harness strap and positioned generally on the rear upper shoulder area of the back section of the strap;
   f) said adjustable first and second shoulder harness straps being crossed and secured together to form a strap crossover section in the back sections of the shoulder harness means;

g) means of securing the first and second ends of the first and second shoulder harness straps to the front and rear portions of the gait belt;

h) first and second upper extremities support ring means on the face sections of the adjustable first and second shoulder harness straps;

i) first and second waist support ring means secured on either side of the gait belt apparatus; and j) restraining strap means for insertion through the upper extremities and waist support ring means and attachment onto a device for holding a patient; whereby said restraining strap means extend from the upper extremities support rings over the shoulder of a patient from front to back, diagonally downward across a back portion of the holding device to a support means opposite the upper extremities support ring, and from a waist support ring means to a rear support post and diagonally across under the patient to a support bar of the holding device opposite the waist support means so that the patient is maintained in an upright position.

12. In combination, the apparatus of claim 11 worn by a patient seated in a wheelchair and the wheelchair and with strap means attached so that the patient is maintained in an upright, seated position, wherein said strap means extend from an upper extremities support ring over the shoulder of a patient from front to back, diagonally downward across a back portion of the wheelchair to a wheelchair support bar opposite the upper extremities support ring, and from a waist support ring means to a wheelchair rear support post and diagonally across under a seat of the wheelchair to a support bar of the wheelchair opposite the waist support ring means.

13. A gait assistance harness apparatus for the assistance of a patient user by a therapist, which apparatus comprises:

a) a gait belt to encircle the waist of a patient user and having a front and a rear section, an adjustable closure means to secure the gait belt in use;

b) a shoulder harness means having first and second shoulder harness straps, each shoulder harness strap having a first end, a second end, a face section and a back section, the first and second ends of the first and second shoulder harness straps secured respectively to the front and back sections of the gait belt;

c) a single, horizontally extended, separate strap belt handle means centrally positioned and secured to the rear section of the gait belt;

d) a pair of vertically extending, separate strap belt handle means centrally located at the rear section of the gait belt and secured to either side of the horizontal belt handle means;

e) said first and second shoulder harness straps being crossed and secured together to form a strap crossover section in the back section of the shoulder harness means;

f) separate strap shoulder handle means located on, secured to and aligned with each of the adjustable first and second shoulder harness straps, and, in use, positioned on the rear upper shoulder area of the back section of the first and second shoulder harness straps, by use of which separate strap shoulder handle means and optionally also with the belt handle means a therapist can assist a patient to walk and by grasping of which a therapist can prevent a patient from accidental falls.

* * * * *